United States Patent [19]

Kaeding et al.

[11] 4,113,788

[45] Sep. 12, 1978

[54] SELECTIVE PRODUCTION OF PARA-XYLENE

[75] Inventors: Warren W. Kaeding, Westfield; Lewis Brewster Young, Kendall Park, both of N.J.

[73] Assignee: Mobil Oil Corporation, New York, N.Y.

[21] Appl. No.: 793,470

[22] Filed: May 3, 1977

Related U.S. Application Data

[63] Continuation-in-part of Ser. No. 638,861, Dec. 8, 1975, Pat. No. 4,034,053.

[51] Int. Cl.² .............................. C07C 3/03; C07C 3/34
[52] U.S. Cl. .................................. 260/673; 260/673.5; 260/668 D; 260/683 R; 208/46
[58] Field of Search ................ 260/673, 673.5, 683 R, 260/668 D; 208/144

[56] References Cited

U.S. PATENT DOCUMENTS

| | | | |
|---|---|---|---|
| 2,971,903 | 2/1961 | Kimberlin et al. | 260/673 |
| 3,271,297 | 9/1966 | Kronig et al. | 208/144 |
| 3,492,220 | 1/1970 | Lempert et al. | 208/144 |
| 3,843,741 | 10/1974 | Yan | 260/673 |

*Primary Examiner*—Delbert E. Gantz
*Assistant Examiner*—C. E. Spresser
*Attorney, Agent, or Firm*—Charles A. Huggett; Raymond W. Barclay

[57] ABSTRACT

A catalytic process is provided for the selective production of para-xylene by contacting, under conversion conditions, an olefinic charge stock with a catalyst comprising a crystalline aluminosilicate zeolite having a silica to alumina ratio of at least about 12, a constraint index, as hereinafter defined, within the approximate range of 1 to 12 and which has combined therewith magnesium in an amount of at least about 0.5 percent by weight.

11 Claims, No Drawings

SELECTIVE PRODUCTION OF PARA-XYLENE

CROSS REFERENCE TO RELATED APPLICATIONS

This application is a continuation-in-part of copending application Ser. No. 638,861, filed Dec. 8, 1975, now U.S. Pat. No. 4,034,053.

BACKGROUND OF THE INVENTION

1. Field of the Invention

This invention relates to a process for converting certain hydrocarbons to a high yield of para-xylene utilizing a magnesium-containing crystalline aluminosilicate zeolite catalyst.

2. Description of the Prior Art

The disproportionation of aromatic hydrocarbons in the presence of zeolite catalysts has been described by Grandio et al. in the *Oil and Gas Journal*, Vol. 69, No. 48 (1971).

U.S. Pat. Nos. 3,126,422; 3,413,374; 3,598,878; 3,598,879 and 3,607,961 show vapor-phase disproportionation of toluene over various catalysts.

Alkylation of aromatic hydrocarbons with an olefin in the presence of a crystalline metallic aluminosilicate having uniform pore openings of about 6 to 15 Angstrom units is described in U.S. 2,290,607. U.S. 3,251,897 describes alkylation of aromatic hydrocarbons in the presence of X- or Y-type crystalline aluminosilicate zeolites, specifically such type zeolites wherein the cation is rare earth and/or hydrogen. U.S. 3,751,504 and 3,751,506 describe vapor phase alkylation of aromatic hydrocarbons with olefins, e.g. benzene with ethylene in the presence of a ZSM-5 type zeolite catalyst.

In these prior art processes, the xylene product produced has the equilibrium composition of approximately 24 percent para, 54 percent of meta and 22 percent of ortho.

The alkylation of toluene with methanol in the presence of a cation exchanged zeolite Y has been described by Yashima et al. in the Journal of Catalysis 16, 273–280 (1970). These workers reported selective production of para-xylene over the approximate temperature range of 200° to 275° C., with the maximum yield of para-xylene in the mixture of xylenes, i.e. about 50 percent of the xylene product mixture, being observed at 225° C. Higher temperatures were reported to result in an increase in the yield of meta-xylene and a decrease in the production of para- and ortho-xylene.

While the above-noted prior art is considered of interest in connection with the subject matter of the present invention, the conversion process described herein, utilizing a catalyst comprising a composite of a crystalline aluminosilicate zeolite and magnesium oxide, which zeolite has a silica/alumina ratio of at least about 12 and a constraint index within the approximate range of 1 to 12, has not, insofar as is known been heretofore described.

Of the xylene isomers, i.e. ortho, meta and paraxylene, meta-xylene is the least desired product, with ortho and para-xylene being the more desired products. Para-xylene is of particular value being useful in the manufacture of terephthalic acid which is an intermediate in the manufacture of synthetic fibers, such as "Dacron". Mixtures of xylene isomers, either alone or in further admixture with ethylbenzene, generally containing a concentration of about 24 weight percent para-xylene in the equilibrium mixture, have previously been separated by expensive superfraction and multistage refrigeration steps. Such process, as will be realized, has involved high operation costs and has a limited yield.

SUMMARY OF THE INVENTION

In accordance with the present invention, there has been discovered a process for the selective production of paraxylene by contacting, under conversion conditions an olefinic charge stock with a catalyst comprising a crystalline aluminosilicate zeolite modified with magnesium. The crystalline aluminosilicate zeolite is essentially characterized by a silica to alumina ratio of at least about 12 and a constraint index within the approximate range of 1 to 12.

The present process comprises conversion of olefins to xylenes in which the proportion of para-xylene isomer is substantially in excess of its normal equilibrium concentration and preferably in excess of 50 weight percent of the xylene product produced in the presence of the specified catalyst at a temperature between about 300° and about 700° C at a pressure between about atmospheric and about 1500 psig utilizing a feed weight hourly space velocity (WHSV) between about 1 and about 1000. The latter WHSV is based upon the weight of catalyst composition, i.e., total weight of active catalyst and binder therefor. The effluent is separated and distilled to remove the desired products, e.g., paraxylene and unreacted product is recycled for further reaction.

DESCRIPTION OF SPECIFIC EMBODIMENTS

The charge stock utilized in the process of this invention contains a predominate proportion of one or more olefins. The olefinic charge preferably contains a $C_2$–$C_{10}$ olefin, or mixtures of such olefins. A representative charge stock suitable for use in the process of the invention, is a stream high in $C_2$–$C_{10}$ olefin content. Thus, ethylene, propylene, butenes, pentenes, hexenes, dienes such as butadiene, pentadienes, cycloolefins such as cyclopentene and cyclohexane, alkyl-substituted cycloolefins such as ethyl cyclopentene, cyclopentadiene and cyclohexadiene can be effectively converted to a high yield of para-xylene utilizing the described catalyst comprising a composite of a specified crystalline aluminosilicate zeolite and magnesium. As sources of the olefin reactant either substantially pure streams of the $C_2$–$C_{10}$ olefin may be employed or refinery or chemical streams high in such reactant, i.e., generally more than 500 volume percent may be used.

The zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e., high silica to alumina ratios, they are very active even when the silica to alumina ratio exceeds 30. This activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g., of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalyst, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions. although puckered structures exist such as TMA offretite which is a known effective zeolite. Also, structures can be conceived due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10 and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having an constraint index in the approximate range of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative results of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value of any given zeolite of interest herein within the approximate range of 1 to 12.

The class of zeolites defined herein is exemplified by ZSM-5, ZSM-11, ZSM-12, ZSM-35, ZSM-38, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Patent 3,832,449, the entire contents of which are incorporated herein by reference.

ZSM-38 is more particularly described in U.S. application Ser. No. 528,060, filed Nov. 29, 1974. This zeolite can be identified, in terms of mole ratios of oxides and in the anhydrous state, as follows:

$$(0.3\text{-}2.5)R_2O : (0\text{-}0.8)M_2O : Al_2O_3 : > 8 \; SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4\text{-}2.5)R_2O : (0\text{-}0.6) \; M_2O : Al_2O_3 : xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d(A) | $I/I_o$ |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminium, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH−/SiO | 0.05–0.5 | 0.07–0.49 |
| H_2O/OH− | 41–500 | 100–250 |
| SiO_2/Al_2O_3 | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH− is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

$$(0.3\text{-}2.5)R_2O : (0\text{-}0.8)M_2O : Al_2O_3 : 8 \; SiO_2$$

wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4\text{-}2.5)R_2O : (0.0.6) \; M_2O : Al_2O_3 : xSiO_2$$

wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | $I/I_o$ |
|---|---|
| 9.6 ± 0.20 | Very Strong – Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |

TABLE II-continued

| d(A) | I/I$_o$ |
|---|---|
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH$^-$/SiO | 0.05–0.5 | 0.07–0.49 |
| H$_2$O/OH$^-$ | 41–500 | 100–250 |
| SiO$_2$Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence or organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combination. Natural minerals which may be so treated include ferrierite, brewsterite, stilbite, dachiardite, epistilbite, heulandite, and clinoptiliolite. The preferred crystalline aluminosilicates are ZSM-5, ZSM-11, ZSM-12, ZSM-38 and ZSM-35, with ZSM-5 particularly preferred.

The catalysts of this invention may be in the hydrogen form or they may be base exchanged or impregnated to obtain ammonium or a metal cation complement. It is desirable to calcine the catalyst after base exchange. The metal cations that may be present include any of the cations of the metals of Groups I through VIII of the Periodic Table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |

| Zeolite | Void Volume | Framework Density |
|---|---|---|
| Heulandite | .39 | 1.69 |
| P | .41 | 1.57 |
| Offretite | .40 | 1.55 |
| Levynite | .40 | 1.54 |
| Erinonite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals.

The crystals of zeolite in a form substantially free of alkali metal, i.e. containing less than about 1.5 weight percent alkali metal and preferably having at least a portion of the original cations associated therewith replaced by hydrogen, are then contacted with a magnesium compound.

Representative magnesium-containing compounds include magnesium acetate, magnesium nitrate, magnesium oxide, magnesium hydroxide, magnesium proprionate, magnesium butyrate, magnesium benzoate, magnesium octoate, magnesium chloride, magnesium bromide, magnesium amide, magnesium carbonate, magnesium chlorate, magnesium citrate and magnesium formate.

Reaction of the zeolite with magnesium compound is effected by contacting the zeolite with such compound. Where the treating magnesium compound is a liquid or solid, such compound can be in solution in a solvent at the time contact with the zeolite is effected. Any solvent relatively inert with respect to the treating compound and the zeolite may be employed. Suitable solvents include water and aliphatic aromatic or alcoholic liquids. Where the magnesium-containing compound is, for example, magnesium octoate, a hydrocarbon solvent, such as n-octane may be employed. The magnesium-containing compound may be used without a solvent, i.e. may be used as a neat liquid.

Prior to reacting the zeolite with the magnesium-containing compound, the zeolite may be dried. Drying can be effected in the presence of air. Elevated temperatures may be employed. However, the temperature should not be such that the crystal structure of the zeolite is destroyed.

Heating of the magnesium-containing catalyst subsequent to preparation and prior to use is also preferred. The heating can be carried out in the presence of oxygen, for example, air. Heating can be at a temperature of about 150° C. However, higher temperatures, i.e. up to about 500° C. are preferred. Heating is generally carried out for 3-5 hours but may be extended to 24 hours or longer. While heating temperatures above about 500° C can be employed, they are not necessary. At temperatures of about 1000° C., the crystal structure of the zeolite tends to deteriorate.

The amount of magnesium incorporated with the zeolite should be at least about 0.5 weight percent. However, it is preferred that the amount of magnesium in the zeolite be at least about 2 percent by weight when the same is combined with a binder, e.g. 35 weight percent of alumina. The amount of magnesium can be as high as about 30 percent by weight or more depending on the amount and type of binder present. Preferably, the amount of magnesium added to the zeolite is between 0.7 and about 25 percent by weight. Without being limited by any theoretical considerations, it is contemplated that magnesium is present in the zeolite in an oxidized state, such as MgO.

The amount of magnesium incorporated with the zeolite by reaction with magnesium-containing compound will depend on several factors. One of these is the reaction time, i.e. the time that the zeolite and the magnesium-containing source are maintained in contact with each other. With greater reaction times, all other factors being equal, a greater amount of magnesium is incorporated with the zeolite. Other factors upon which the amount of magnesium incorporated with the zeolite is dependent include reaction temperature, concentration of the treating compound in the reaction mixture, the degree to which the zeolite has been dried prior to reaction with the magnesium-containing compound, the conditions of drying of the zeolite after reaction of the zeolite with the treating compound, and the amount and type of binder incorporated with the zeolite.

In practicing the desired conversion process it may be desirable to incorporate the modified zeolite in another material resistant to the temperatures and other conditions employed in the conversion process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the sub-bentonites and the kaolins commonly known as Dixie, McNamee-Georgia and Flordia clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided modified zeolite and inorganic oxide gel matrix may very widely with the zeolite content ranging from between about 1 to about 99 percent by weight and more usually in the range of about 5 to about 80 percent by weight of the composite.

The process of this invention is conducted such that conversion is carried out in the vapor phase by contact in a reaction zone, such as, for example, a fixed bed of catalyst, under effective conversion conditions, said catalyst being characterized as above-described and preferably hydrogen exchanged such that a predominate portion of its exchangeable cations are hydrogen ions. In general, it is contemplated that more than 50 percent and preferably more than 75 percent of the cationic sites of the crystalline aluminosilicate zeolite, above-described, will be occupied by hydrogen ions.

The conversion process described herein may be carried out as a batch-type, semi-continuous or continuous operation utilizing a fixed or moving bed catalyst system. A preferred embodiment entails use of a fluidized catalyst zone wherein the hydrocarbon charge is passed concurrently or countercurrently through a moving fluidized bed of the catalyst. The fluidized catalyst after use is conducted to a regeneration zone wherein coke is burned from the catalyst in an oxygen-containing atmosphere, e.g., air, at an elevated temperature, after which the regenerated catalyst is recycled to the conversion zone for further contact with the toluene feed.

The following examples will serve to illustrate the process of the invention without limiting the same.

EXAMPLE 1

A quantity of 2 grams of catalyst which contained 65% microcrystalline (0.02–0.05 micron) HZSM-5 and 35% alumina binder was placed in a quartz microreactor and tested for its ability to catalyze the conversion of various olefinic feeds to aromatic products. The conditions of reaction and results obtained are set forth in Table III below.

TABLE III

| | | | | Weight Percent in Product | | | | |
|---|---|---|---|---|---|---|---|---|
| Feed | Temp., °C | WHSV, hr$^{-1}$ | Conversion of Feed, % | $\geq C_5$ | Aromatics | Xylenes in Aromatics | Para in Xylenes | Ortho in Xylenes |
| Propylene | 400 | 3.1 | 100 | 55 | 28 | 39 | 24.2 | 22.5 |
| Propylene | 350 | 3.1 | 99 | 70 | 16 | 36 | 24* | 23 |
| Propylene | 450 | 3.1 | 100 | 51 | 34 | 37 | 24* | 22 |
| Ethylene | 400 | 2.1 | 100 | 55 | 27 | 35 | 24.3 | 22 |
| 1-Hexene | 400 | 3.0 | 100 | 53 | 29 | 39 | 24* | 19 |

*Estimated from data obtained.

It will be seen from the above results that the xylene isomer mixture correspond substantially to that of equilibrium composition.

EXAMPLE 2

A quantity of 2 grams of HZSM-5 of about 2 micron crystal size without a binder was tested for its ability to catalyze the conversion of olefinic feeds to aromatics. The conditions of reaction and results obtained are summarized below in Table IV.

EXAMPLE 3

Six grams of the ammonium form of microcrystalline (0.02–0.05 micron) ZSM-5 zeolite was pressed into wafers, crushed and screened to a size of 14–20 mesh. It was then added to a solution of 5.25 grams of magnesium acetate tetrahydrate in 15 ml of water heated to about 90° C. The slurry was allowed to stand at this temperature for about 17 hours. It was then poured into a crystallizing dish and placed in an oven at 110° C for a period of six hours to remove most of the water. The oven temperature was increased to level out at 200° C and allowed to stand for 1.5 hours. It was then transferred to a furnace at 500° C, in air, and permitted to stand for 15.5 hours. The theoretical amount of magnesium in the resulting product was 8.5 percent by weight.

EXAMPLE 4

The catalyst of Example 3 (1.8 grams) was tested in a quartz microreactor for its ability to transform olefinic charge stocks to aromatic products. Conditions of reaction and results are shown in Table V below:

TABLE V

| | | | | Weight Percent in Product | | | | |
|---|---|---|---|---|---|---|---|---|
| Feed | Temp., °C | WHSV, hr$^{-1}$ | Conversion of Feed, % | $\geq C_5$ | Aromatics | Xylenes in Aromatics | Para in Xylenes | Ortho in Xylenes |
| Propylene | 400 | 4.2 | 91 | 57 | 10 | 39 | 96 | 2 |
| Propylene | 450 | 4.2 | 85 | 44 | 10 | 38 | 94 | — |
| Propylene | 500 | 4.2 | 75 | 31 | 8 | 38 | 94 | 2 |
| Ethylene | 400 | 2.8 | 86 | 50 | 13 | 35 | 93 | — |
| 1-Hexene | 400 | 8.9 | 89 | 62 | 4 | 7 | >95 | — |

From the above results, it will be evident that use of the magnesium-modified ZSM-5 catalyst afforded a xylene product rich in the valuable para isomer.

EXAMPLE 5

Six grams of the ammonium form of ZSM-5 of about 2 micron crystal size was pressed into wafers, crushed and screened to a size of 14–20 mesh. It was added to a solution of 7.0 grams of magnesium acetate tetrahydrate in 15 ml of water and permitted to stand for approximately 16 hours at room temperature. It was then poured into a crystallizing dish and placed in an oven at 110° C for about 7 hours. The temperature was then increased to level out at 200° C keeping the sample in the oven for a total of 1.5 hours. It was thereafter transferred to a 500° C oven, in air, for a period of 21.5 hours. The theoretical amount of magnesium in the resulting product was 11.1 percent by weight.

TABLE IV

| | | | | Weight Percent in Product | | | | |
|---|---|---|---|---|---|---|---|---|
| Feed | Temp., °C | WHSV, hr$^{-1}$ | Conversion of Feed, % | $\geq C_5$ | Aromatics | Xylenes in Aromatics | Para in Xylenes | Ortho in Xylenes |
| Propylene | 350 | 3.1 | 96 | 51 | 10 | 33 | 43 | 15 |
| Ethylene | 400 | 2.1 | 97 | 52 | 25 | 38 | — | 19 |

EXAMPLE 6

The catalyst of Example 5 (2.0 grams) was tested for its ability to convert olefinic charge stocks to aromatics. The conditions of reaction and results are summarized below in Table VI.

TABLE VI

| Feed | Temp., °C | WHSV, hr$^{-1}$ | Conversion of Feed, % | Weight Percent in Product | | | | |
|---|---|---|---|---|---|---|---|---|
| | | | | $\geq C_5$ | Aromatics | Xylenes in Aromatics | Para in Xylenes | Ortho in Xylenes |
| Propylene | 350 | 3.1 | 98 | 70 | 17 | 40 | 72 | 10 |
| Ethylene | 400 | 2.1 | 99 | 51 | 29 | 35 | 44 | 14 |

From the above results it will be seen that use of the magnesium-modified ZSM-5 catalyst served to increase the production of para-xylene.

EXAMPLE 7

Microcrystalline (0.02–0.05 micron) HZSM-5 was impregnated with magnesium acetate in a manner similar to that of Example 3 to yield a catalyst which contained 10.85 weight percent magnesium.

EXAMPLE 8

A sample of the catalyst of Example 7 was employed for the conversion of propylene. A feed of propylene was passed over such catalyst at a temperature of 400°–600° C at one atmosphere pressure at a weight hourly space velocity of 3. The conditions of reaction and results are set forth in Table VII below.

TABLE VII

| Run No. | Temp, °C. | Hr On Stream | Propylene Conv., % | Selectivity, Wt. % | | | | |
|---|---|---|---|---|---|---|---|---|
| | | | | % Para-Xylene in Xylenes | % Xylenes in Aromatics | Aromatics | Ethylene | Ethylene + $C_5$-Olefins |
| 1 | 400 | 1.0 | 97.1 | 85.5 | 33.1 | 20.2 | 1.0 | 11.0 |
| 2 | 500 | 2.0 | 87.8 | 71.3 | 34.4 | 22.6 | 6.5 | 22.4 |
| 3 | 500 | 6.5 | 86.1 | 73.3 | 33.3 | 19.6 | 5.9 | 25.9 |
| 4 | 500 | 22.5 | 71.0 | 75.7 | 28.5 | 8.1 | 7.7 | 45.0 |
| | | | Catalyst calcined at 500° C., 0.5 Hr.; 550° C., 0.5 Hr.; 600° C., 3 Hrs. | | | | | |
| 5 | 500 | 1.5 | 90.7 | 73.1 | 34.6 | 26.9 | 5.0 | 16.5 |
| 6 | 600 | 3.0 | 74.4 | 68.1 | 20.0 | 28.8 | 23.1 | 40.2 |
| 7 | 600 | 6.0 | 61.1 | 70.0 | 18.1 | 27.7 | 27.8 | 54.2 |
| 8 | 600 | 10.5 | 56.8 | 71.6 | 18.2 | 19.2 | 25.5 | 57.2 |
| 9 | 600 | 23.5 | 24.4 | 76.4 | 7.4 | 10.9 | 21.0 | 58.2 |

It will be seen from the above results that ethylene yield increased with temperature whereas the yield of para-xylene selectivity decreased. In every instance, however, the amount of para-xylene was very substantially greater than its equilibrium concentration of 24 percent.

It is to be understood that the foregoing description is merely illustrative of preferred embodiments of the invention of which many variations may be made by those skilled in the art within the scope of the following claims without departing from the spirit thereof.

We claim:

1. A process for conversion of olefins to xylenes in which the proportion of para-xylene isomer is substantially in excess of its normal equilibrium concentration which comprises contacting, under conversion conditions, including a temperature between about 300° and about 700° F, a pressure between about atmospheric and about 1500 psig and a weight hourly space velocity of between about 1 and about 1000, an olefinic charge stock in which the $C_2$–$C_{10}$ olefin content is more than 50 volume percent with a catalyst consisting essentially of a crystalline aluminosilicate zeolite having a silica to alumina ratio of at least about 12 and a constraint index within the approximate range of 1 to 12, said catalyst having combined therewith magnesium in an amount of at least about 0.5 percent by weight, as a result of contact of said zeolite with a magnesium compound in the liquid phase; cooling the resulting product and separating paraxylene therefrom.

2. The process of claim 1 wherein said proportion of para-xylene isomer is in excess of 50 weight percent of the xylene product produced.

3. The process of claim 1 wherein said charge stock is a substantially pure stream of the $C_2$–$C_{10}$ olefin.

4. The process of claim 1 wherein the magnesium content is between about 0.7 and about 25 weight percent.

5. The process of claim 1 wherein said crystalline aluminosilicate zeolite is ZSM-5.

6. The process of claim 5 wherein ZSM-5 is predominantly in the hydrogen form.

7. The process of claim 5 wherein ZSM-5, having magnesium combined therewith, is present in combination with a binder therefor.

8. The process of claim 1 wherein said zeolite, having magnesium combined therewith, is present in combination with a binder therefor.

9. The process of claim 1 wherein said charge stock is propylene.

10. The process of claim 1 wherein said charge stock is ethylene.

11. The process of claim 1 wherein said charge stock is hexene.

* * * * *

UNITED STATES PATENT AND TRADEMARK OFFICE
CERTIFICATE OF CORRECTION

PATENT NO. : 4,113,788
DATED : September 12, 1978
INVENTOR(S) : WARREN W. KAEDING and LEWIS BREWSTER YOUNG It is certified that error appears in the above-identified patent and that said Letters Patent are hereby corrected as shown below:

Column 2, line 49, "500 volume percent may be used." should read --50 volume percent may be used.--
Column 7, line 38, "$SiO_2Al_2O_3$" should read --$SiO_2/Al_2O_3$--
Column 8, line 17, "impregnated to obtain" should read --impregnated to contain--
Column 10, line 59, "inorganic oxide gel matrix may very widely with" should read --inorganic oxide gel matrix may vary widely with--

Signed and Sealed this

Twenty-seventh Day of March 1979

[SEAL]

Attest:

RUTH C. MASON
Attesting Officer

DONALD W. BANNER
Commissioner of Patents and Trademarks